United States Patent
Psaros et al.

[11] Patent Number: 6,152,133
[45] Date of Patent: Nov. 28, 2000

[54] ANAESTHETIC DELIVERY SYSTEM

[75] Inventors: Georgios Psaros, Tullinge; Pär Emtell, Vällingby, both of Sweden

[73] Assignee: Siemens Elema AB, Sundbyberg, Sweden

[21] Appl. No.: 09/343,178

[22] Filed: Jun. 30, 1999

[30] Foreign Application Priority Data

Jul. 17, 1998 [SE] Sweden ................................ 9802568

[51] Int. Cl.⁷ .................................................... A62B 7/10
[52] U.S. Cl. .................. 128/205.12; 128/203.12
[58] Field of Search ...................... 128/203.12, 204.13, 128/204.14, 204.15, 204.16, 205.12

[56] References Cited

U.S. PATENT DOCUMENTS

| | | | |
|---|---|---|---|
| 3,592,191 | 7/1971 | Jackson | 128/204.16 |
| 3,713,440 | 1/1973 | Nicholes | 128/205.12 |
| 4,617,924 | 10/1986 | Heim et al. | 128/204.23 |
| 4,991,576 | 2/1991 | Henkin et al. | 128/205.13 |
| 5,044,361 | 9/1991 | Werner et al. | 128/204.16 |
| 5,471,979 | 12/1995 | Psaros et al. | 128/205.28 |
| 5,487,380 | 1/1996 | Grabenkort | 128/204.15 |
| 5,694,924 | 12/1997 | Cewers | 128/205.12 |

FOREIGN PATENT DOCUMENTS 505 217   7/1997   Sweden.
WO 98/11931   3/1998   WIPO.

*Primary Examiner*—Aaron J. Lewis
*Attorney, Agent, or Firm*—Hill & Simpson

[57] ABSTRACT

An anaesthetic delivery system has a ventilation arrangement with an inspiration gas pathway for conducting inspiration gas to a patient and an expiration gas pathway for conducting expiration gas away from the patient, and a filter element serially connected to both the inspiration and the expiration gas pathways. The filter element retains anaesthetic from expiration gas passing therethrough and releases the retained anaesthetic into inspiration gas passing therethrough. A supply of flushing gas is communicable with the filter element to flush the retained anaesthetic from the system without passing to the patient.

7 Claims, 2 Drawing Sheets

ANAESTHETIC DELIVERY SYSTEM

BACKGROUND OF THE INVENTION

1. Field of the Invention

The present invention relates to an anaesthetic delivery system and in particular to a system of the type wherein gaseous anaesthetic expired by a patient is re-used by introducing it into gas intended to be inspired by the patient.

2. Description of the Prior Art

A patient anaesthetic delivery system is described in U.S. Pat. No. 5,471,979 wherein fresh respiration gas passes through an adsorption filter to take up adsorbed anaesthetic, which was collected from gas expired by the patient that also passed through the filter. In this manner expensive anaesthetic, which would otherwise be lost, can be reused. This system has a common inspiration/expiration gas pathway for the delivery and the discharge of anaesthetic and respiration gases to and from the patient and the adsorption filter is disposed in this common pathway, for the adsorption and desorption of anaesthetic gas. A second pathway, which bypasses the adsorption filter, is also provided for the delivery of anaesthetic and/or respiration gases to the patient without passing through the adsorption filter. Practically, the efficiency (i.e. the percentage of expired anaesthetic retained by the filter) of the adsorption filter will be required to be fixed at less than 100% (typically 80%). Some anaesthetic within the expired gas will then always pass through the filter to be lost from the respiration system. This is necessary in order to make the system more responsive to user required changes in the concentration of anaesthetic to be delivered to the patient.

SUMMARY OF THE INVENTION

It is an object of the present invention to provide an anaesthetic delivery system in which the amount of anaesthetic retained from the expired gas can be varied on demand.

The above object is achieved in an anaesthetic delivery system in accordance with the invention having an inspiration gas pathway for conducting inspiration gas to a patient and an expiration gas pathway for conducting expiration gas away from the patient, and a filter element serially connected to both the inspiration and the expiration gas pathways, the filter element retaining anaesthetic from expiration gas passing through the filter and releasing the retained anaesthetic into inspiration gas passing through the filter, and having a supply of flushing gas communicable with the filter element to flush the retained anaesthetic without exposing the patient to anaesthetic during a flushing procedure.

By providing a source of flushing gas which is adapted to flush anaesthetic from the filter element and away from the patient, i.e. without being taken up by the patient, the amount of anaesthetic retained in the system can be varied. Furthermore by controlling the amount of flushing gas passed through the filter some or none of the retained anaesthetic can be allowed to remain within the filter element for subsequent supply to the patient. Additionally, the anaesthetic filter element can be made 100% efficient, since flushing will rapidly remove unwanted anaesthetic from the element as and when required.

Preferably, the respiration gas is used as the supply of flushing gas and is controlled to flush the retained anaesthetic into the expiration line at a site downstream of the filter element, (downstream and upstream are used herein to describe locations with respect to the direction of flow of the relevant gas). Thus existing components of the known anaesthetic delivery system, or perhaps slightly modified versions thereof, can be used so that the number of additional components required to provide the system of the present invention can be reduced. By flushing the anaesthetic into the expiration line after the filter element, an existing apparatus for preventing exhaled anaesthetic from entering the immediate environment may be employed.

The supply of flushing gas may be provided during the expiration phase of a patient's breathing cycle to thereby lower the risk of flushed anaesthetic being taken up by the patient.

DESCRIPTION OF THE PREFERRED EMBODIMENTS

Figure 1:
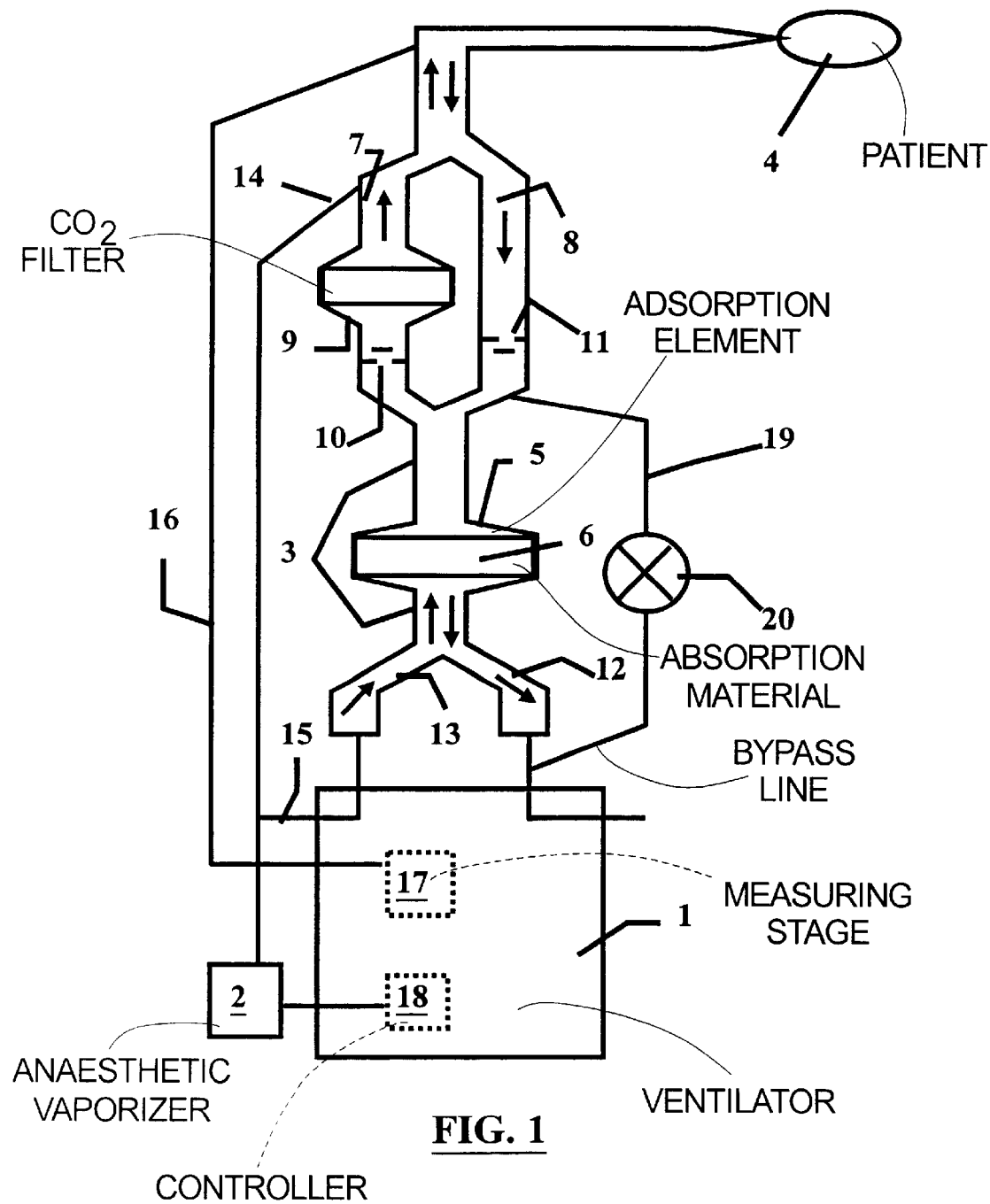
FIG. 1 is a schematic illustration of a system according to the present invention.

As shown in FIG. 1, an anaesthetic delivery system includes a patient ventilator 1 operably connected to an anaesthetic vaporizer 2. The vaporizer 2 may alternatively be disposed integral with the ventilator 1. Also included is a common inspiration/expiration gas line 3 for the delivery and the discharge of anaesthetic and respiration gases to and from a patient 4. An adsorption element 5, which contains adsorption material 6 such as carbon for example in the form of wood or coconut shell charcoal, for the adsorption and desorption of anaesthetic gases, is arranged in the common line 3. The line between the patient 4 and the adsorption element 5 is partially divided into an inspiration branch 7 and an expiration branch 8 and a carbon dioxide absorption filter 9 is placed in the inspiration branch 7. One-way valves 10,11 are disposed in the inspiration branch 7 and the expiration branch 8 respectively, with the valve 11 in the inspiration branch 7 being positioned downstream of the adsorption element 5, between it and the filter 9. The free end of the common line 3 is formed into a Y-coupling, with one branch 12 being connected via the ventilator 1 to an evacuation system (not shown) for the expired gas, and with the other branch 13 being connected to the ventilator 1 for delivering, as needed, fresh respiration gas to the patient 4. The delivery system further includes a gas line 14 for delivering gaseous anaesthetic from the anaesthetic vaporizer 2 to the inspiration branch 7 downstream of both the anaesthetic adsorption element 5 and the $CO_2$ filter 9. A further gas line 15 is connected to the line 13 and to the respirator 1 for delivering, as needed, fresh respiration gas to the patient 4, bypassing the element 5.

A gas line 16 is provided to conduct a sample of inspiration gas to a measuring stage 17. A signal corresponding to the concentration of anaesthetic in the inspiration gas is supplied by the measuring stage 17 to a controller 18 which is operably connected within the system to physically control the delivery of respiration and anaesthetic gases dependent of the signal from the measuring stage 17 in order to achieve a desired gas mixture at the patient 4.

A gas bypass line 19 is also provided which, when the controllable valve 20 is open, permits gas in the expiration line to be conducted to the evacuation system without passing through the adsorption element 5.

The controller 18 is also adapted to control the operation of the valve 20 to open the valve during an expiration phase of the patient's breathing cycle when respiratory gas is supplied as a flushing gas through the element 5 via the lines 13 and 3 in a manner to ensure that the valve 10 does not open. The one-way valve 10 may, for added safety, be replaced with a controllable valve similar to that 20 in the bypass line 19 and operable by the controller 18 to close during the expiration phase in which flushing gas is to be supplied.

During a normal respiration cycle the valve 20 is closed and expiration gas must then pass through the element 5 during the expiration phase. The anaesthetic gas, supplied during a previous inspiration phase, which the patient 4 expires is then adsorbed by the filter material 6 of the adsorption element 5 while the remainder of the expiration gas passes through the common line 2 and the branch 12, via the ventilator 1, into the evacuation system. Only in the inspiration phase of the respiration cycle is respiration gas supplied from the ventilator 1, via the common line 2 and, because the one-way valve 11 is in a blocking state, the inspiration branch 7 to the patient 4. Inspiration gas thus passes through the adsorption element 5 where the previously adsorbed anaesthetic gas is desorbed and mixes with the respiration gas to be supplied to the patient 4.

When the element 5 requires flushing, for example when a reduced concentration or no anaesthetic is required, then during the appropriate expiration phase or phases the controller 18 opens the valve 20 to couple the bypass line 19 into the system so that gas flowing in towards the element 5, from the patient side bypasses the element 5. Respiratory gas is supplied from the ventilator 1 during these expiration phase or phases and passes through the element 5 at a pressure which will not cause the one-way valve 10 in the inspiration branch 7 to open. This respiration gas, together with the anaesthetic desorbed from the element 5 is thus caused to pass through the bypass line 19 and into the evacuation system together with the expired gas from the patient 4.

Figure 2:
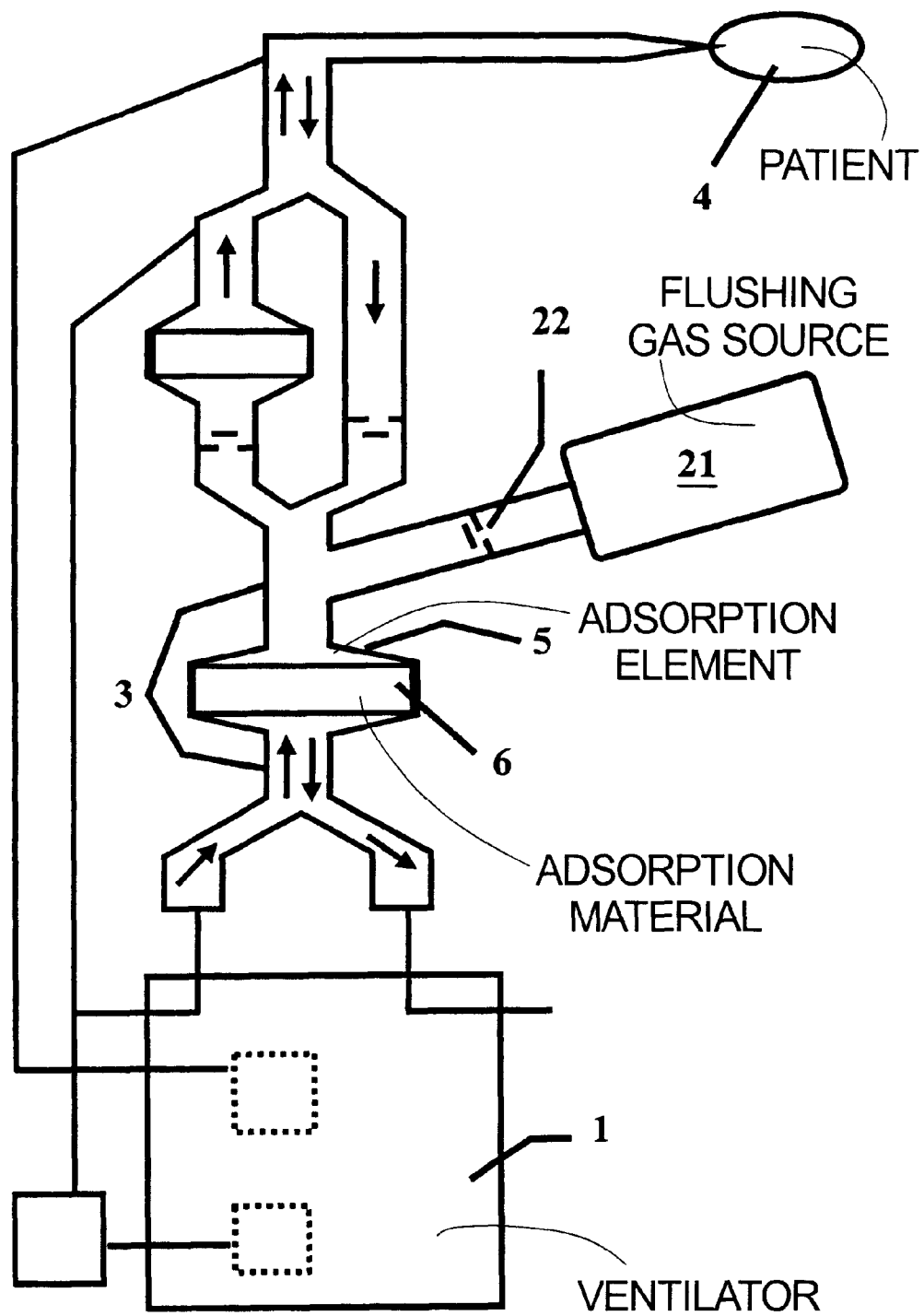
FIG. 2 shows a modification of the system of FIG. 1 to provide an alternative flushing gas system.

FIG. 2 shows the delivery system of FIG. 1 modified to include an alternative flushing system. In FIG. 2 the components that are common to both the embodiment of FIG. 1 and that of FIG. 2 are given the same reference numerals.

As shown in FIG. 2, a dedicated source of flushing gas 21, which may for example be an cylinder of pressurized air, is connected via a one-way valve 22 to the common gas line 3 at a location such that flushing gas will pass from the source 21, through the material 6 of the adsorption element 5 toward the ventilator 1 and away from the patient 4, i.e. in the normal flow direction of the expiration gas. When flushing of the element 5 is required, gas from the source 21 is forced through the element 5 during an expiration phase of the patient's breathing cycle to remove retained anaesthetic therefrom into the evacuation system together with the expired gas.

Those skilled in the art will appreciate that the flushing gas supply 21 of FIG. 2 may also be placed on the opposite side of the element 5. In this case the bypass line 19 and valve 20 of FIG. 1 may be added and operated in a manner analogous to the above described situation where flushing gas is supplied from the ventilator 1.

Although the invention is described herein with reference to a so called "open-loop" delivery system where expired gas is not re-circulated and is passed out of the system it will be appreciated by those skilled in the art that the invention may also be used in so called "closed-loop" systems where expiration gas is re-circulated to be re-used by a patient. For example considering the embodiment of FIG. 1, the expiration line 12 downstream of the adsorption filter element 5 may be made selectively coupled to the inspiration line 13 upstream of the adsorption filter element 5 to provide a closed-loop ventilator system when the lines 12, 13 are coupled.

Although modifications and changes may be suggested by those skilled in the art, it is the intention of the inventors to embody within the patent warranted hereon all changes and modifications as reasonably and properly come within the scope of their contribution to the art.

We claim as our invention:

1. An anaesthetic delivery system comprising:
   a ventilator having an intubation system including an inspiration gas pathway adapted for conducting inspiration gas to a patient and an expiration gas pathway adapted for conducting expiration gas away from a patient;
   a filter serially connected to said inspiration gas pathway and to said expiration gas pathway, said filter retaining an anaesthetic, as retained anaesthetic, from expiration gas passing through said filter and releasing the retained anaesthetic into inspiration gas passing through said filter; and
   a supply of flushing gas communicable with said filter to flush the retained anaesthetic from the filter without exposing a patient to the retained anaesthetic.

2. An anaesthetic delivery system as claimed in claim 1 wherein said supply of flushing gas is connected to said inspiration gas pathway upstream of said filter.

3. An anaesthetic delivery system as claimed in claim 2 wherein said ventilator contains said supply of flushing gas.

4. An anaesthetic delivery system as claimed in claim 2 further comprising a bypass gas pathway and a controllable valve operable to couple and decouple said filter element from the expiration gas pathway through said bypass gas pathway, said supply of flushing gas flushing the retained anaesthetic through said bypass gas pathway.

5. An anaesthetic delivery system as claimed in claim 1 wherein said supply of flushing gas directs flushing gas through said filter in a direction of flow of said expiration gas through said filter.

6. An anaesthetic delivery system as claimed in claim 1 wherein said supply of flushing gas operates in chronological synchronization with a breathing cycle of a patient to direct a pulse of flushing gas through said filter during an expiration phase of said breathing cycle.

7. An anaesthetic delivery system as claimed in claim 1 wherein said expiration gas pathway downstream of the filter is coupled to the inspiration pathway upstream of said filter to produce a closed-loop ventilation system.

* * * * *